(12) United States Patent
Ben-Arye et al.

(10) Patent No.: US 9,011,497 B2
(45) Date of Patent: Apr. 21, 2015

(54) BONE ANCHORING SYSTEM

(75) Inventors: Asaf Ben-Arye, Zichron Yaakov (IL); Yuval Shezifi, Haifa (IL); Arnon Epstein, Korazim (IL)

(73) Assignee: Scorpion Surgical Technologies Ltd., Misgav Business Park (IL)

( * ) Notice: Subject to any disclaimer, the term of this patent is extended or adjusted under 35 U.S.C. 154(b) by 1343 days.

(21) Appl. No.: 12/667,535

(22) PCT Filed: Jul. 2, 2008

(86) PCT No.: PCT/IL2008/000913
§ 371 (c)(1),
(2), (4) Date: Jun. 1, 2010

(87) PCT Pub. No.: WO2009/004625
PCT Pub. Date: Jan. 8, 2009

(65) Prior Publication Data
US 2010/0305700 A1    Dec. 2, 2010

Related U.S. Application Data

(60) Provisional application No. 60/929,553, filed on Jul. 2, 2007.

(51) Int. Cl.
*A61B 17/88* (2006.01)
*A61B 17/70* (2006.01)
*A61B 17/00* (2006.01)

(52) U.S. Cl.
CPC ....... *A61B 17/70* (2013.01); *A61B 2017/00469* (2013.01)

(58) Field of Classification Search
CPC . A61F 2002/444; A61F 2/442; A61F 2/4455; A61F 2/446; A61F 2/4465; A61F 2/447
USPC ......... 606/278, 279, 246–264, 148, 103, 105; 623/17.11, 17.16
See application file for complete search history.

(56) References Cited

U.S. PATENT DOCUMENTS

| 4,135,506 A | 1/1979 | Ulrich |
| 4,790,303 A | 12/1988 | Steffee |

(Continued)

OTHER PUBLICATIONS

ESSR dated Mar. 1, 2013 in corresponding European patent application No. 08763669.2.

(Continued)

*Primary Examiner* — Mary Hoffman
*Assistant Examiner* — Christina Negrellirodriguez
(74) *Attorney, Agent, or Firm* — Daniel J. Swirsky; AlphaPatent Associates Ltd.

(57) ABSTRACT

Methods and apparatus for connecting to a bone, which avoid the use of bone screws. A triangular shaped modular implant is used, with two sides of the structure and their respective vertex secured generally within the bone, with the base of the triangle outside the bone. These two arms, whether straight or arcuate, are cannulated, and are held together at their distal ends by a tightened cable that runs through both of the arms. The proximal ends of these arms are connected to a base side that completes the triangular structure. The device may be inserted into a vertebra and the base used for vertebral fusion. Alternatively, the arms themselves may be used to stabilize and fixate adjacent vertebrae, by insertion through adjacent vertebrae trans-segmentally. In the latter case, the vertex may be within the intervertebral space or within the vertebral body close to the intervertebral space.

12 Claims, 13 Drawing Sheets

(56) References Cited

U.S. PATENT DOCUMENTS

| | | |
|---|---|---|
| 5,928,267 A | 7/1999 | Bonutti et al. |
| 6,045,551 A | 4/2000 | Bonutti |
| 6,050,998 A | 4/2000 | Fletcher |
| 6,607,530 B1 | 8/2003 | Carl et al. |
| 6,923,811 B1 | 8/2005 | Carl et al. |
| 7,458,981 B2 * | 12/2008 | Fielding et al. ............... 606/279 |
| 2004/0117019 A1 * | 6/2004 | Trieu et al. ................. 623/17.11 |
| 2004/0127907 A1 * | 7/2004 | Dakin et al. .................... 606/72 |
| 2005/0125066 A1 * | 6/2005 | McAfee ..................... 623/17.16 |
| 2005/0149030 A1 * | 7/2005 | Serhan et al. ................... 606/73 |
| 2005/0267481 A1 | 12/2005 | Carl et al. |

OTHER PUBLICATIONS

PCT Int'l Search Report and Written Opinion of the ISA, mailed Nov. 14, 2008 in PCT/IL08/00913.

\* cited by examiner

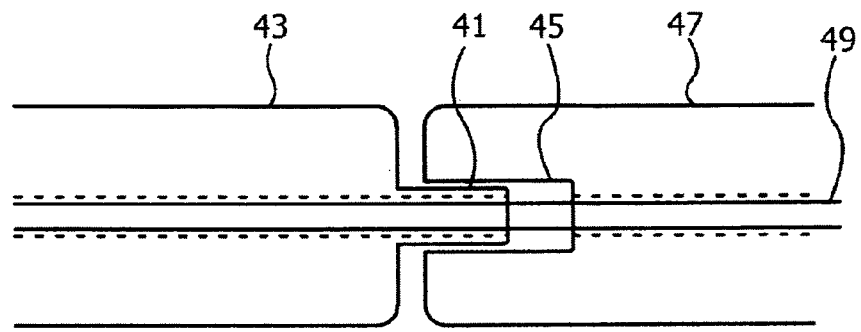
Fig. 4B
Fig. 4C
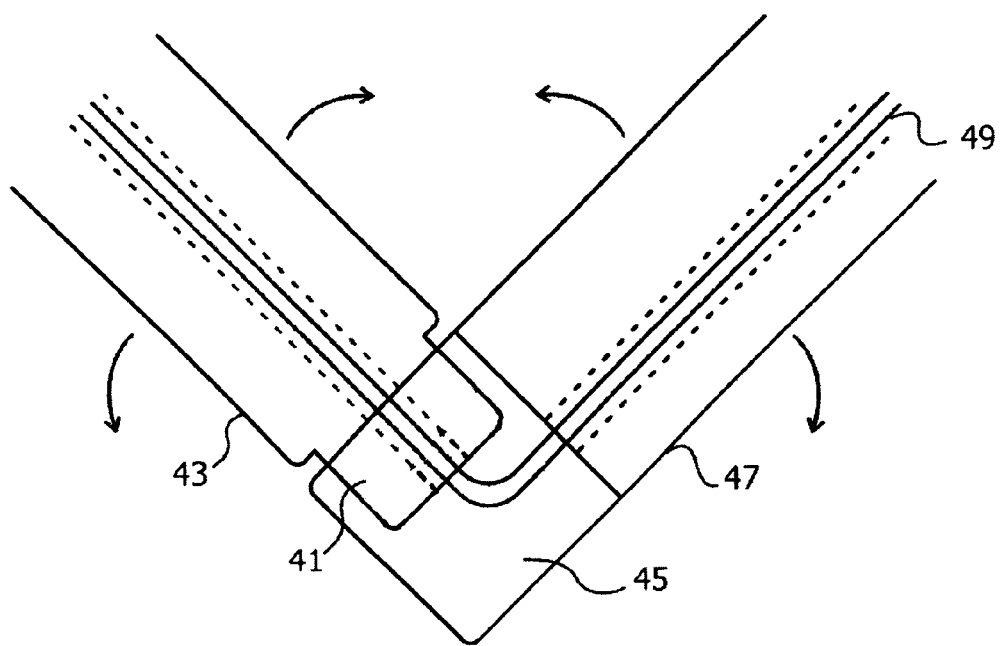

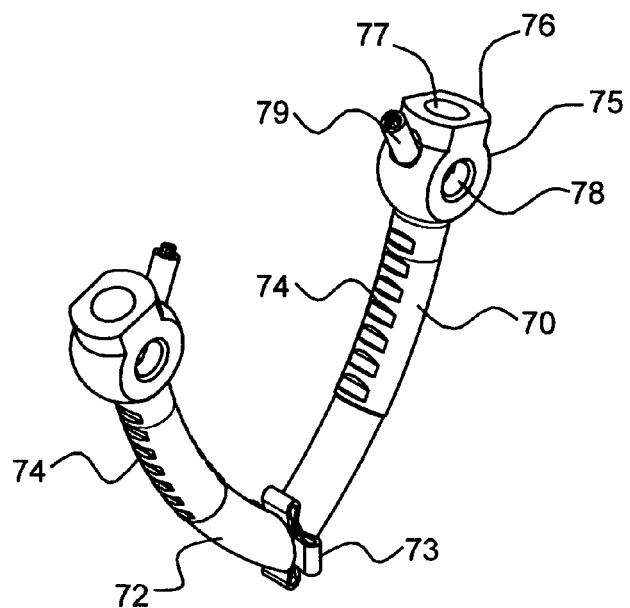
FIG. 7
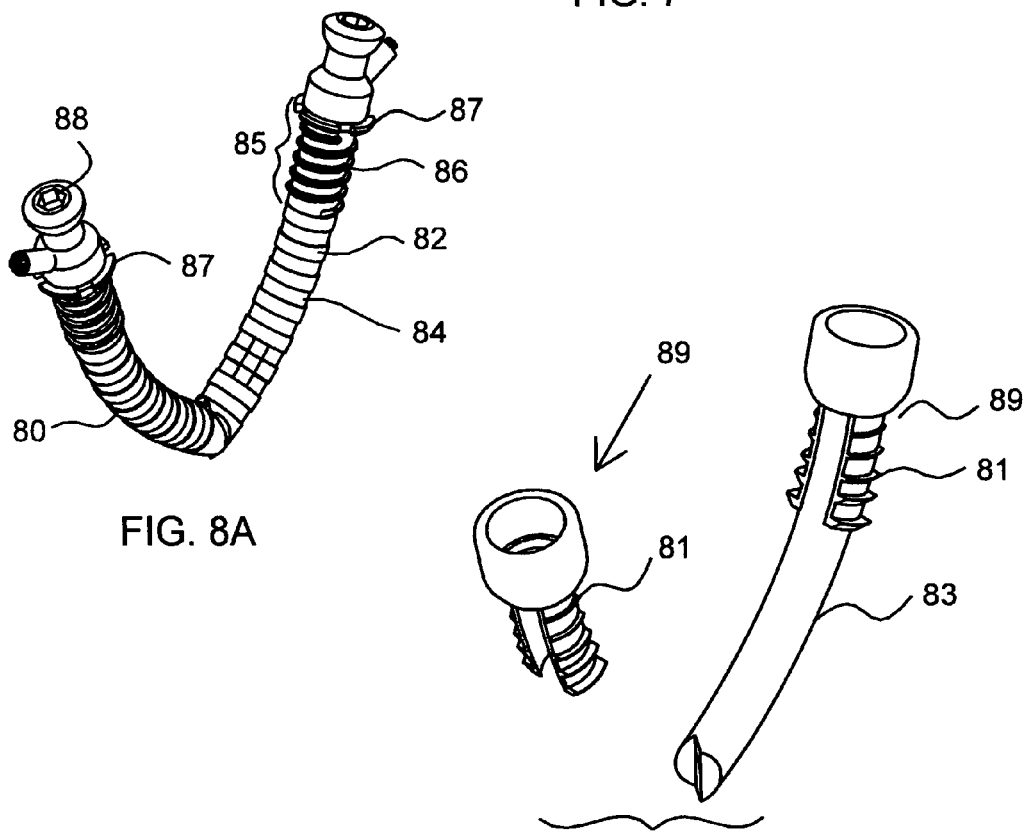
FIG. 8A
FIG. 8B

BONE ANCHORING SYSTEM

CROSS-REFERENCE TO RELATED APPLICATIONS

This application is a U.S. National Phase Application under 35 U.S.C. 371 of PCT International Application No. PCT/IL2008/000913, which has an international filing date of Jul. 2, 2008, and which claims benefit from U.S. Provisional Patent Application No. 60/929,553, filed Jul. 2, 2007, the contents of which are herein incorporated by reference in their entirety.

FIELD OF THE INVENTION

The present invention relates to the field of systems and methods for making connections between bones or bone parts, and especially for spinal use in making rigid connections with vertebrae.

BACKGROUND OF THE INVENTION

There are many methods known in the art for stabilizing bones, or for connecting portions of bones or different bones. Many of these methods use screws inserted into the bone structure and connecting elements held by these screws. It is also known in the art to use arcuate elements to fixate bones or to connect separate bones or bone parts. Such arcuate elements have a number of advantages over conventional methods of orthopedic fixing, using screws tapped into the parts to be fixed. One of the most important advantages is that the arcuate element, by virtue of its shape, provides positive resistance to linear pull out without the need to rely on the gripping strength of screw threads.

There are a number of prior art publications which describe the orthopedic uses of arcuate elements for connecting adjacent bones or bone parts together. Among these publications U.S. Pat. Nos. 6,607,530 and 6,923,811 to A. Carl et al., show arcuate elements for connecting adjacent vertebrae. According to one method described therein, the arcuate elements are held in place by virtue of their curved shape, being made as a press fit into the prepared arcuate aperture, or by virtue of the addition of a compressible material or bone growth materials, to ensure that the element is firmly wedged into its channel, or by the use of externally applied screws to fix the arcuate elements into the arcuate aperture.

In US Patent Application Publication No. 2005/0267481, also to A. Carl et al., there is shown an arcuate element for connecting adjacent vertebrae, which is secured to the vertebral bodies using interlocking screws that traverse the rod and penetrate the vertebra at angles that avoid sensitive neurological structures. However, this arrangement requires the drilling of additional holes into the vertebrae for the interlocking screws, with the additional danger of penetrating sensitive neurological structures.

In U.S. Pat. No. 5,928,267 to P. Bonutti et al, there is described, inter alia, an arcuate channel cut into two parts of a fractured bone, with a suture running through the channel, such that tightening and bonding the suture draws the bone parts together.

In U.S. Pat. No. 4,790,303 to A. D. Steffee, there is shown a barbed arcuate fastener for driving into adjacent bone parts, for securing a bone graft between the bone parts. One embodiment shows a pair of such fasteners, driven into the bone portions in opposite directions, and with their protruding end portions connected by a tensioned wire, to assist in retaining the fasteners in position. Specifically, if one of the fasteners tends to move out of the bone portions in a direction, opposite to the direction in which it was driven, it would be resisted by the other fastener which would have to move in the same direction to that which it was driven and further into the bone portions. However, the wire appears to play no part in stabilizing the rigidity of the structure of the two fasters, since it is attached flexibly to their outer ends, and is only described as resisting their mutual withdrawal.

Each of the prior art inventions mentioned above has some aspect which may be disadvantageous in use. There therefore exists a need for a new apparatus and method for fixing or joining bone parts together, which is simple in application, provides a stable connection with the bone, and may provide either a rigid structure to the bone or bones themselves, or a sound connection to other parts such as dynamic stabilizers, and without undue danger to the subject during implementation.

The disclosures of each of the publications mentioned in this section and in other sections of the specification, are hereby incorporated by reference, each in its entirety.

SUMMARY OF THE INVENTION

The present invention seeks to provide a new system and method for fixation to bones or for anchoring bone portions to each other, or for connecting bones to each other, based on the use of rigid triangular structures. The system utilizes a triangular structure generally comprising three separate elements which make up the three sides of the triangular structure. Two sides of the triangular structure are generally located within the bone or bones, their included apex being generally located distally to the bone or bones, or within the bone or bones. The third side of the triangular structure is generally external and proximal to the bone or bones. In particular cases, the triangular structure may comprise only two separate elements located within the bone or bones, and the third base element of the structure is made up of the bone structure itself, this constituting a "virtual third side" to the triangle. The elements of the triangular structure are held rigidly in place by means of a wire or thread passed down the two sides of the triangular structure that meet at the apex, and tensioned such that the ends at the apex are held firmly in place. Such tensioning may be conveniently done at the proximal ends of the elements of these two sides of the triangular structure.

The triangular structure is especially useful for fixation between vertebrae, or connection to vertebrae, and these examples are generally used throughout this application to illustrate the proposed system. However, it is to be understood that vertebral use is only one example of the use of the devices described in this disclosure, and that this application is not meant to be limited to spinal use, but can equally well be used for other orthopedic fixation or connection, whenever the shape of the bone or bones to be treated allows its use. The term triangle is interpreted in this disclosure to include generally 3-sided elements, whether the "sides" are straight lines, as in a conventional geometric triangle, or whether they are arcuate, or any combination thereof. Furthermore, there is no need for symmetry, and according to further examples of the system, one of the two internal sides of the triangle can be straight, and the other arcuate, or both can be arcuate but with different radii, or with different length, or both.

The triangular structures described in this disclosure may be used for fixation of a single bone, or for anchoring to a single bone, to provide a rigid anchor at the bone. This can typically be used for providing external connections to the bone, by means of which other elements may be connected. In such examples, the first two sides of the triangular structure preferably pass through two regions of the bone to be fixated, with those two sides being firmly connected at their apex (or vertex), and the third side of the triangle is preferably rigidly connected to those ends of the first two sides opposite to the joined apex ends. The third side may be executed by means of a physically separate external connector rod making up the third side. Alternatively, the third side can be a "virtual third side", generated by firmly fixing to the bone each of the ends of those first two sides opposite to the joined apex ends, such that the intervening bone between those two opposite ends of the first two sides constitutes the structure of the third side. Once such a structure has been formed in a single vertebra, the outer portion of the structure can be used as support points for attaching other elements for connection to other bone structures, such as to other neighboring vertebrae. Typically, a triangular system having all three of its apexes joined, provides an efficient load sharing structure in which all of the sides take part, significantly reducing local stress and therefore reducing loosening and breakage of either bone or of the implant elements. By this means, it is possible to perform conventional spinal fusion using connecting rods, but with the connecting rods attached to the triangular structure instead of by means of screws driven into the pedicles. This generally can provide more strength, rigidity, durability and resistance to loosening, besides being a generally safer procedure.

There exist in spinal surgery, methods and systems for motion preservation, whereby, rather than fusing neighboring vertebrae by which relative motion is compromised, the relative motion between vertebra is preserved, often by means of replacement facet joints using posterior dynamic stabilization elements. Such systems generally rely on pedicle screws for connection to the vertebra. Since such systems are intended for long dynamic use, and are subject to continuous dynamic stresses as the vertebrae move relative to each other, the need to resist loosening, breakage, or pull-out is even more important than for fusion attachments. According to further implementations, triangular structures of with arcuate elements may be used for fixing the elements of the motion preservation replacement joints to the vertebrae, resulting in a more robust fixing method, with longer, trouble-free lifetime, thus substantially improving such motion preservation systems.

For those examples where the structure is used for connection of two bones, or bone portions, the first two sides of the triangular structure pass through the two bones to be anchored together, with those two sides being firmly connected at their apex, and the third side of the triangle is connected rigidly to those ends opposite to the joined apex ends of the first two sides. The third side may be executed by means of a physically separate external connector element, such as a rod, making up the third side. Alternatively, also in these cases, the third side can be a virtual third side, generated by firmly fixing each of the ends of those first two sides opposite to the joined apex ends, to one of the bone portions, such that the intervening bone portions constitute the structure of the third side.

Furthermore, when applied to spinal surgery, methods and structures using arcuate-shaped elements, such as is described in this application, enable posterior entry of the structural elements, with their distal ends anchored at the anterior portions of the vertebral body or disc region, yet without encroaching on the spinal cord channel because of the curved shape of the elements. This aspect represents a substantial improvement over the prior art use of arcuate elements in spinal surgery, where anterior entry is generally used in order to avoid approaching the spinal channel. Such anterior access is generally achieved only by substantial surgical procedures. The posterior arcuate element structures described in this application, on the other hand, can be inserted using minimally invasive surgical procedures on the patient's back.

According to additional aspects of the present invention, the first two sides of the triangular structures of the present invention are made of cannulated arms, and are held in contact with each other at their apex by means of a flexible cable, cord, wire, thread or suture (generally called wire or cable hereinafter, and thuswise claimed, but understood to include any flexible pulling member) passed through the cannulated arms, and tightened so as to pull the ends of the arms together at the apex. The combination of cable and cannulated arms arranged in a triangular structure provides a convenient mechanism for constructing such a rigid triangular structure, having a unique combination of complementary advantages not available to either component separately. The cable is flexible and can easily be deployed into a pre-tunneled aperture. It may be further used as a guide to lead the cannulated arms, though the arms may alternatively be put in place before the cable is threaded. However, the cable is generally of small diameter and if used alone as an anchor, it may dig into the bone when pulled-out. Therefore, the use of a cable alone in such applications is disadvantageous. Cannulated arms are strong and can provide solid attachment to eternal elements or components connected to them. Arcuate shapes can, by their nature, be used as an orientation mechanism to the tunneling tool, using the arcuate arm as part of the drilling mechanism that pushes a flexible drill in a curved direction during its entry. However, as stand alone devices, they are vulnerable to pull-out. The combination of cannulated arms and cable is immune to the above disadvantages, since each component of this combination makes up for the disadvantages of the another—the cable connects the two arms inside the bone and reduces the pull-out problem, while the cannulated arms provide strength, and, due to their comparatively large diameter and their rigidity, they do not dig into the bone but rather distribute the loads.

A further advantage of the use of the wire connected triangular structure is that at any time during the lifetime of the implant, if it is necessary to remove the implant elements, this can be done simply by releasing the wire at the proximal end of an insert, whereupon the arcuate arms can be slid or worked out of their channels without the need for surgical intervention at or surgical access to the joint point of the elements at the apex.

The terms proximal and distal are used in this application according to the generally accepted convention regarding implants, such that the location of the point concerned is described as distal or proximal relative to the point of insertion into the subject's body. Thus, the distal end of an element is the end of the element penetrated furthest into the body, while the proximal end is that end closest to the insertion point.

There is thus provided in accordance with different examples for implementing the present invention, a triangular orthopedic structure, comprising:

(i) a first and a second tubular element disposed for at least a major part of their length within a bone of a subject, from a first and a second entry point to the bone, to a junction at which the distal ends of the tubular elements meet, and (ii) a wire threaded through both of the tubular elements between their proximal ends, such that when the wire is tensioned, the distal ends of the first and second tubular elements become tightened onto the junction, such that the first and second tubular elements generate a rigid structure within the bone.

Whereas the previously described triangular orthopedic structure is intended for insertion into a single bone, other exemplary devices of this application include orthopedic structures for insertion between two bones, such structures comprising:

(i) a first tubular element disposed for at least a major part of its length within a first bone of a subject, and a second tubular element disposed for at least a major part of its length within a second bone of a subject, the distal ends of the first and second tubular elements meeting at a junction, and the proximal ends being disposed in the vicinity of first and second entry points to the first and second bones respectively, and (ii) a wire threaded through the tubular elements between their proximal ends, such that when the wire is tensioned, the distal ends of the first and second tubular elements become tightened onto the junction, such that the first and second tubular elements generate a rigid structure between the bones.

In either of the above-described structures, the tensioned wire may be anchored at the proximal ends of the tubular elements, and this may be achieved by any one of bonding, crimping, clamping and bolting.

Additionally, at least one of the tubular elements may be arcuate in form, in which case, it may be disposed in a preformed arcuate passage in the bone.

The proximal ends of the tubular elements may either be joined by means of a rigid connecting element, forming a third side of the triangular structure, or they may be attached to a posterior part of the bone, such that the posterior part of the bone forms the third side of the triangular structure. Such a rigid connecting element may be adapted for anchoring an external element to the bone, or alternatively, an external element may be anchored to the proximal ends of the tubular elements. Such an external element may be a component of a motion preserving inter-vertebral joint.

In any of the above described single bone structures, the bone may be vertebra of the subject, and the triangular structure may then be an anchor for fixation of the vertebra to an adjacent vertebra. In any of the above described vertebral structures, at least one of the first and second entry points may located at a pedicle of the vertebra.

Any of the above-described structures may further comprise a rounded element having a smooth surface disposed on the wire at the junction, such that the first and second tubular elements abut against the rounded element when the wire is tensioned.

Another example implementation can be such that the meeting of the distal ends of the first and second tubular elements at the junction may comprise a ball and socket type of joint, each of the first and second tubular elements having one component of the ball and socket joint. In either of the previous examples, the distal ends of the first and the second tubular elements can pivot at the junction, such that tensioning of the wire can adjust the orientation and position of the structure before the wire is locked.

Alternatively, the distal end of one of the tubular elements may have a tongue-like projection, and the distal end of the other of the tubular elements may then have a slot into which the tongue-like projection fits, such that the tubular elements can mutually pivot to a desired orientation before the wire is tensioned.

Still other example implementations involve structures further comprising a voluminous element disposed at the junction, such that when the wire is tensioned, the voluminous element is crushed and at least some of its parts become deployed beyond the diameter of the tubular elements. The deployed parts of the crushed voluminous element can then provide additional anchoring of the structure in the bone.

Yet other implementations may involve structures in which at least part of the external surface of at least one of the first and second tubular elements is profiled such that the part of surface provides additional anchorage of the structure in the bone.

Additionally, in more exemplary structures, at least one of the tubular elements may further comprise a straight threaded rotatable sleeve mounted on a proximal part of its length, such that when the sleeve is rotated, the thread becomes screwed into the bone. The screwing of the thread into the bone may then be operative to pull the element into the bone.

Other example implementations involve the use of first and second tubular elements whose distal ends comprise meshing teeth structures, such that the elements cannot perform mutual rotation.

In those of the above structures described for use in a pair of vertebra, the first and the second tubular elements may be disposed on the same side of the spine of the subject.

Additionally, first and second triangular structures as described hereinabove, may be use to define another orthopedic structure, in which each of the first and second structures has its tubular elements disposed on opposite sides of the spine of the subject.

In those examples involving structures for use in a pair of vertebra, the first and the second entry points may be disposed on opposite sides of the spine of the subject, such that the first and second tubular elements are diagonally disposed relative to the spine of the subject. In such cases, each of the first and second structures may have its first and the second entry points disposed such that the tubular elements of the first structure, and the tubular elements of the second structure, are disposed such that they have crossed orientations.

In all of those exemplary implementations involving structures for use in a pair of vertebra, the first and second structures may be connected by external elements, such that the first and second bones are anchored to each other.

Additionally, other aspects of the invention described in this disclosure may involve a method for stabilizing adjacent vertebrae of a spine, comprising the steps of:

(i) forming a first arcuate passage in a first one of the vertebrae from a pedicle entry point to an intra-vertebral anterior position, (ii) forming a second arcuate passage in the first vertebrae from the opposite pedicle entry point to meet the intra-vertebral anterior position, (iii) threading a wire between the pedicle entry points, (iv) sliding an arcuate cannulated member into each of the arcuate passages, (v) tensioning the wire such that the ends of the arcuate members become tightened onto a junction at the intra-vertebral anterior position, (vi) repeating the steps on a second vertebra adjacent to the first vertebra, and (vii) fixating the first and second vertebra by rigidly connecting at least one pair of pedicular ends of the cannulated members between the first and second vertebrae.

Such a method may further comprise the step of attaching the wire to the ends of the arcuate cannulated members after tensioning of the wire.

In the above described methods, the step of threading a wire between the pedicle entry points may be performed before the step of sliding an arcuate cannulated member into each of the arcuate passages, such that the arcuate cannulated members are slid over the wire, or alternatively, it can be performed after the step of sliding an arcuate cannulated member into each of the arcuate passages, such that the wire is threaded through the arcuate cannulated members.

Another example implementation can involve a method for stabilizing adjacent vertebrae of a spine, comprising the steps of:

(i) forming a first arcuate passage in a first one of the vertebrae from a pedicle entry point to an anterior position,
(ii) forming a second arcuate passage in a second vertebra adjacent to the first vertebra, from a pedicle entry point on the same lateral side of the vertebra as that of the first vertebra, to meet the anterior position of the first arcuate passage,
(iii) threading a wire between the pedicle entry points,
(iv) sliding arcuate cannulated members down each of the arcuate passages,
(v) tensioning the wire such that the ends of the arcuate members become tightened onto a junction at the anterior position,
(vi) repeating the steps on the opposite lateral side of the first and second vertebra, and
(vii) fixating the first and second vertebra by rigidly connecting at least one pair of pedicular ends of the cannulated members between the first and second vertebrae.

Such a method may further comprise the step of attaching the wire to the ends of the arcuate cannulated members after the tensioning of the wire. Furthermore, the anterior position may be inter-vertebral, or intra-vertebral.

Furthermore, in the above described methods, the step of threading a wire between the pedicle entry points may be performed before the step of sliding an arcuate cannulated member into each of the arcuate passages, such that the arcuate cannulated members are slid over the wire, or alternatively, it can be performed after the step of sliding an arcuate cannulated member into each of the arcuate passages, such that the wire is threaded through the arcuate cannulated members.

Still other example implementations involve an orthopedic element for insertion into a bone, the element comprising:
(i) a distal portion having an arcuate shape, and
(ii) a threaded rotatable sleeve having a straight shape, the sleeve being mounted on a proximal part of the element, such that when the element is inserted into a channel in the bone and the sleeve is rotated, the thread becomes screwed into the bone.

For such an element, the screwing of the thread into the bone may be used to pull the element into the channel. This screwing of the thread into the bone may also assist in anchoring the element into the bone.

Finally, according to yet another exemplary device described in this disclosure, there is provided a tool for generating an arcuate passageway in a bone, comprising:
(i) an arcuate hollow drill guide,
(ii) a drill bit on a flexible drilling cable passing through the drill guide,
(iii) a counter probe laterally displaceable from the distal end of the drill guide, and
(iv) an adjustment assembly for adjusting the position of the counter probe relative to the drill guide, such that when the counter probe is inserted into a pilot hole in the bone, the tool can be adjusted such that the arcuate passageway is generated at a predetermined position therefrom.

When using such a tool, the bone may be a vertebra, and the pilot hole may be formed in a first pedicle of the vertebra, and the adjustment assembly can be adjusted such that the arcuate passageway is formed down a second pedicle of the vertebra. In such a situation, the counter probe may have an arcuate shape which fits into an arcuate shaped pilot hole in the first pedicle, such that the tool is stabilized while the arcuate passageway is formed down the second pedicle.

BRIEF DESCRIPTION OF THE DRAWINGS

The present invention will be understood and appreciated more fully from the following detailed description, taken in conjunction with the drawings in which:

FIGS. 4B and 4C illustrate schematically a pivot joint in which a tongue at the end of one arm fits into a slot in the end of the other arm, enabling pivoting action;

FIG. 7 shows schematically arcuate arms with ridged surface, and a method of attachment of the distal ends of the arcuate arms using a polyaxial mounting head;

FIG. 8A shows a pair of arcuate elements with a rotatable screw sleeve for screwing the inserts into their passage, while FIG. 8B shows an alternative method of anchoring inserts, using an expandable toothed collar;

DETAILED DESCRIPTION

Figure 1:
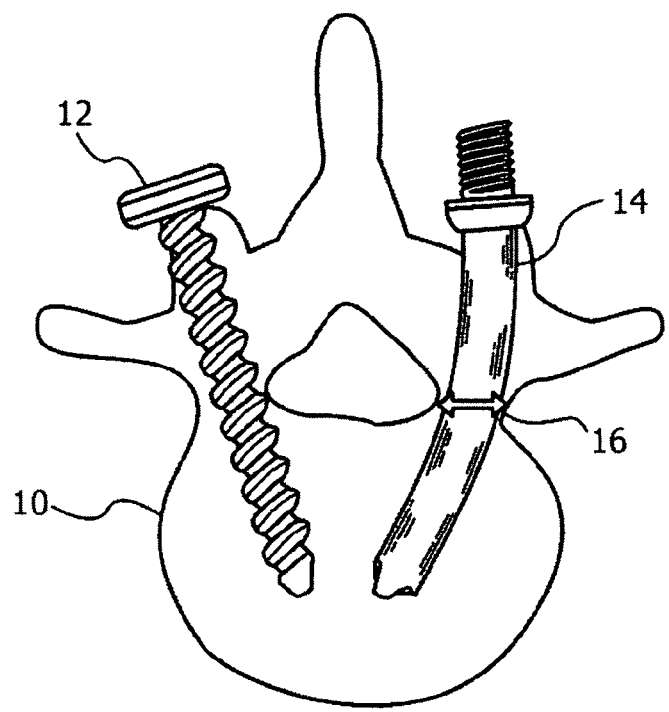
FIG. 1 is a schematic drawing of a vertebra, comparing a prior art screw and an arcuated arm, both inserted into the vertebra through a pedicle.

Reference is now made to FIG. 1, which is a schematic cross sectional drawing of a vertebra 10, comparing a prior art screw 12 and an arcuate arm 14 of the type described in this specification, both inserted into the vertebra through a pedicle. The screw dimensions are, by definition, a balance between the size of its threads and its core (the minor diameter). The threads provide pull-out resistance and the core provides the strength necessary to withstand bending, stretching or shearing. In addition, a screw advances forward by rotation and therefore needs to be straight. A trans-pedicular route in the vertebra is basically governed by the tunnel of the pedicle which limits the diameter of the structure that passes through it and to a certain degree, its course about the midsection of the pedicle. The need not to deviate from this course further limits the diameter of the screw. Thus, for a given screw member, its strength is determined by the material of which it is made, and the limitations implied by the location into which it is driven.

In contrast to this, an arcuate arm does not need to have any threads and therefore a larger, and thus stronger core 16 can be inserted through a trans-pedicular tunnel into the vertebra. Because of its shape, the arcuate arm prevents rotation, and needs to be slid into a pre-tunneled aperture.

Figure 2:
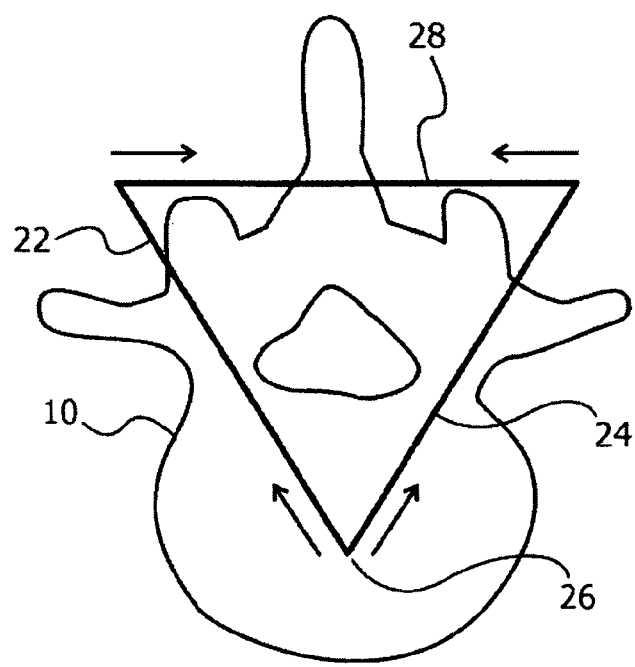
FIG. 2 illustrates schematically a vertebra showing the geometry of a triangular structure as an anchoring means in the vertebra.

Reference is now made to FIG. 2, which illustrates schematically a vertebra showing the geometry of a triangular structure as an anchoring means in a vertebra. Two of the sides 22, 24 and their vertex 26 are embedded in the vertebra. The base side 28 and its vertices are outside the bone, completing the triangular structure. The triangular structure as an anchor is resistant to pull-out even if straight sides are used, since stress applied to any of its components is shared by the entire structure.

Figure 3:
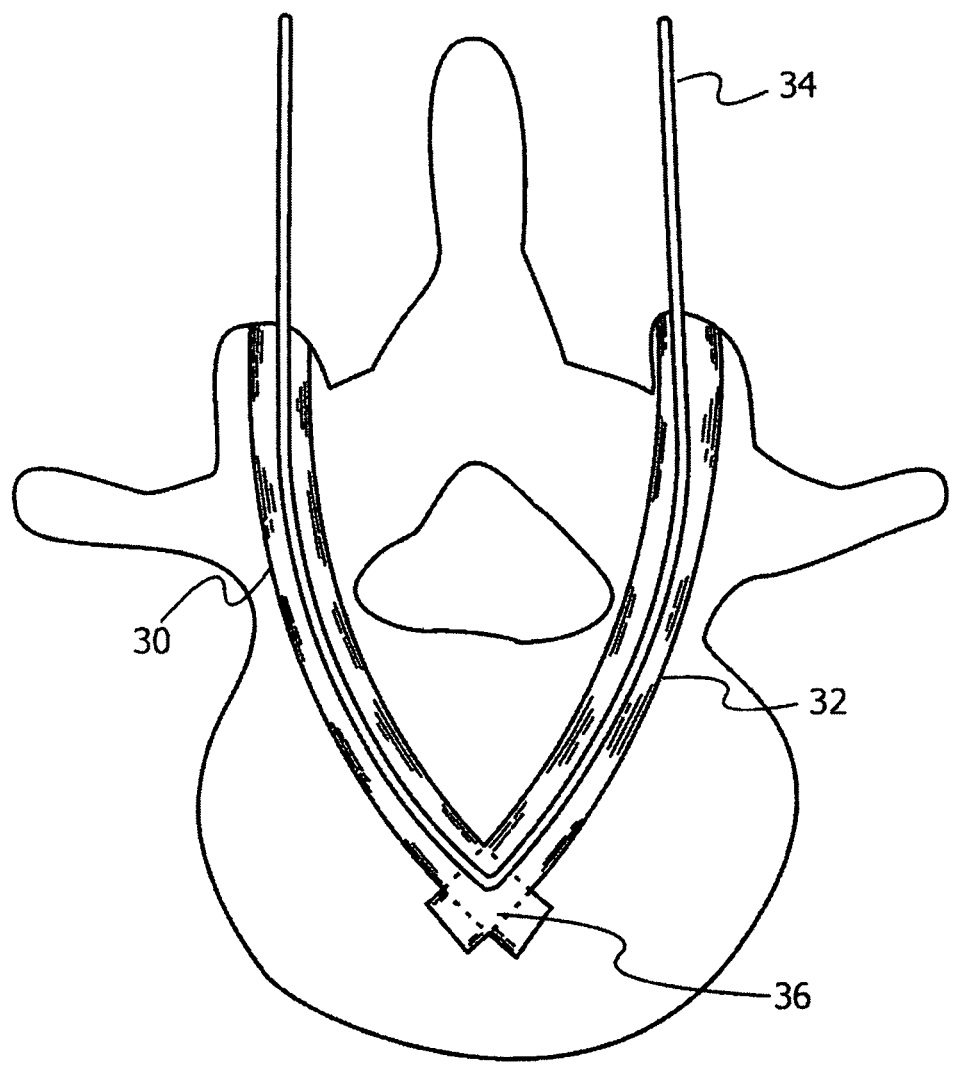
FIG. 3 is a schematic illustration of a vertebra with a drilled passage that is the combination of two intersecting arcuated tunnels.

Reference is now made to FIG. 3 which is a schematic illustration of a vertebra with a passage that is the combination of two intersecting arcuated tunnels 30, 32. The two tunnels create a vertex at their intersection point 36. A cable 34 is threaded through the combined passage. The cable may be connected directly to a structure at the posterior side of the vertebra, but due to its relative small diameter, it may dig into the bone under tension and hence not provide good pull-out resistance.

Figure 4A:
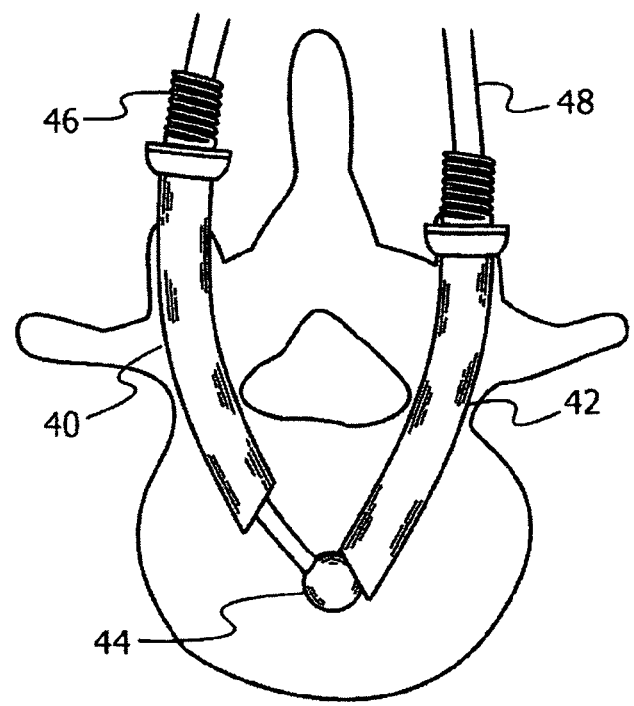
FIG. 4A schematically illustrates a vertebra with two arcuated arms inserted into pre-tunneled passages, such as those shown in the example of FIG. 3.

Reference is now made to FIG. 4A which schematically illustrates an exemplary implementation in which the triangular structure is used directly as an anchoring method for stabilizing adjacent vertebrae of the spine, as an alternative to the commonly used spinal fixation screws and rods. In this example, the pseudo-triangle structure is generated by the creation of a channel, either straight or arcuate, through each of the adjacent vertebrae to be connected, the insertion of two sides of the triangle components through the channels, and the assembly of the triangular structure by completion of the third side, as mentioned above. In more detail, the method includes the steps of creating two intersecting tunnels in the vertebrae, one in each vertebra, the tunnels being straight or arcuate. The tunnels can be formed by mechanical drilling, or by any other suitable form of excavation, such as laser drilling or ablation. The tunnels are formed from two entrance points, one on each of the vertebrae, and are aligned at such an angle and follow such a course that they intersect at a distal point, creating a roughly V-shaped channel, either straight like a Capital letter V, or curved like a script letter v. The entrance points may be advantageously located at the pedicles, which by their nature, have roughly the mutual angle and course such that a tunnel can be drilled down them through the osseous canal, into the vertebral body, and towards the vertebra's anterior side at its midline. The combined course of the opening is the combination of the two tunnels, straight or arcuate, such that an apex is formed at their intersection point. Once the tunnels have been drilled, a flexible cable may be passed serially through the combined channels, so that it protrudes at both ends from the two entrance points. Two cannulated arms may then be inserted over the cable, one into each of the two tunnels. The cannulated arms may be straight or arcuate, to match the tunnel shape. Each of the cannulated arms is inserted into its respective tunnel from its respective entrance, and is pushed down the bone tunnels until the two meet at the intersection point of the tunnels, where the arms make contact at their distal ends and create the vertex of the triangle.

Referring now to the details of the example shown in FIG. 4A, the two arcuate arms 40, 42 are inserted into a pre-tunneled passage, such as that shown in FIG. 3. The arms make contact at their distal ends, at which point a ball-and-socket structure 44 may be used to assist in stabilizing the connection between the arms at the vertex. The left hand arcuate arm 40 is shown slightly withdrawn from its final position to illustrate the form of this ball-and-socket structure. The internal cable 46 is shown threaded through the two arcuate arms and tightened. Although the example of FIG. 4A is shown with a separate spherical ball to provide the sliding pivot contact between the arcuate arms, it is to be understood that any other mechanical interface which provides such a pivoting joint may also be used. For instance, the end itself of one of the arcuate arms could be in the form of a socket, while that of its companion member could have a hemispherical ball shape.

The use of a cable for fixing the triangular structure of the present invention has an added advantage in that it allows for unlocking the connection between the arcuate arms when it is desired to demount the structure and retrieve the implant, even after a number of few years.

According to another preferred embodiment, shown schematically in FIGS. 4B and 4C, a pivot joint may be used for enabling pivoting action, while fixing the arms once the wire is tightened. In the embodiment shown, FIG. 4B shows the apex viewed from the base of the triangular structure, while FIG. 4C is a cross sectional view of the pivot joint. A tongue-like projection 41 at the end of one arm 43 fits into a slot 45 at the end of the other arm 47. A cable 49 running through bores in each of the arms, is used to tighten the triangular structure. The arrows in FIG. 4C show how each arm can pivot to achieve the desired orientation before the tensioned cable is fixed.

The combination of the two arms and tightened cable creates a horseshoe structure that constitutes two sides of the triangular structure of this embodiment, and which resists pull-out. The extending portion of the arms external to the bone is preferably threaded 48 to facilitate connection to a posterior structure. This posterior structure could be a connecting element between the arms, operative as the base side of the triangular structure, but could also simultaneously function as the binding points to other structures, such as a vertebral fusion rod, or another anchoring means.

Figure 5A:
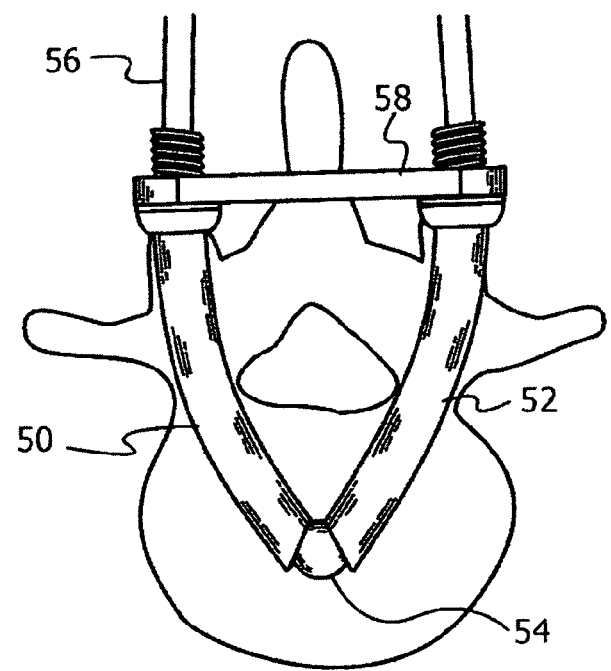
FIG. 5A schematically illustrates a vertebra with a complete pseudo-triangle structure formed therein, including the base side of the triangle.

Reference is now made to FIG. 5A which schematically illustrates a vertebra with the pseudo-triangle structure of FIG. 4A shown completely assembled. The cable can be tightened and locked at the proximal ends of the side arms that protrude from the bone. Tightening of the cable ensures contact between the cannulated arms at the apex, but does not impose the angle between them, leaving the final angle to be determined by the surgeon when adjusting and locking the cable. A base side can then be attached to the two proximal (posterior) ends of the two cannulated arms to complete the triangle. Those parts of the triangle structure that remain outside the vertebra, besides providing good rigidity, can be used for attachment to stabilizing elements such as for motion preservation, spinal posterior dynamic stabilization or for fixation of adjacent vertebrae. A triangular implant, constructed and operative according to these aspects of this invention, having one apex embedded in the vertebra, constitutes an anchoring solution which is resistant to pullout and with the added advantage that it inherently distributes stress applied to any of its components to the entire structure. This triangular structure would thus appear to have advantages over prior art anchoring methods where a closed structure may not be provided, and where the strength of the inserted structure may be dependent on the anchoring strength of individual elements.

Referring now to the details of the exemplary structure shown in FIG. 5A, the triangle may consist of two arcuated and cannulated arms 50, 52, abutted at the distal end to create the apex 54 of the triangle. The arms are slid over a cable 56, such that it runs inside the internal lumen generated by the arcuate arms, and that is locked or bonded or crimped or attached by any other suitable method to the proximal ends of the arms that extend out from the posterior side of the vertebra. A base side 58 is shown connected to the proximal ends to complete the triangular structure. This triangular structure then constitutes a firm and rigid base which can be used for performing spinal fusion by attaching the vertebra to its neighbor or neighbors by means of rigid connecting elements mounted onto the base side 58, most simply at the threaded ends of the arcuate arms 50, 52, but also possibly by attachment directly to the cross member 58.

Figure 5B:
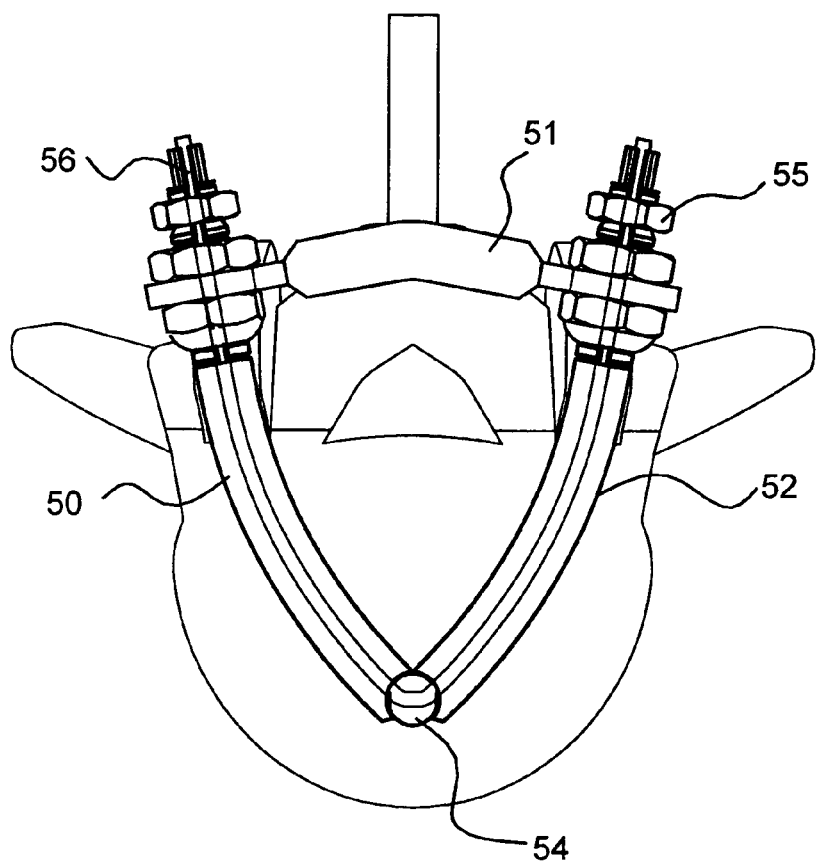
FIG. 5B is a cross sectional view of the vertebra of FIG. 5A including a screw-operated, cable tensioning and fixing arrangement.

Reference is now made to FIG. 5B which is a schematic horizontal cross-sectional representation of the vertebra of FIG. 5A, showing a slightly curved base side 51 screwed onto the proximal ends of the arcuate cannulated arms. In addition, a screw-operated, cable tensioning and fixing arrangement 55 is shown at the proximal end of the arcuate arms, such that the structure shape adjustment and cable tensioning can be readily performed. As an alternative to the screw tensioning device, the cable 56 can be tensioned by any means, such as manually, and held at its predetermined position by means of a bondable material, whether heat activated to melt the bonding material, or chemically bonded, such as an epoxide-like compound, or by crimping, as will be described hereinbelow, or by clamping, by any other suitable means.

Reference is now made to FIGS. 6 to 10 which show details of more examples of methods and components for fixing arcuate elements of the triangular structures described in this disclosure, into a vertebra.

Figure 6:
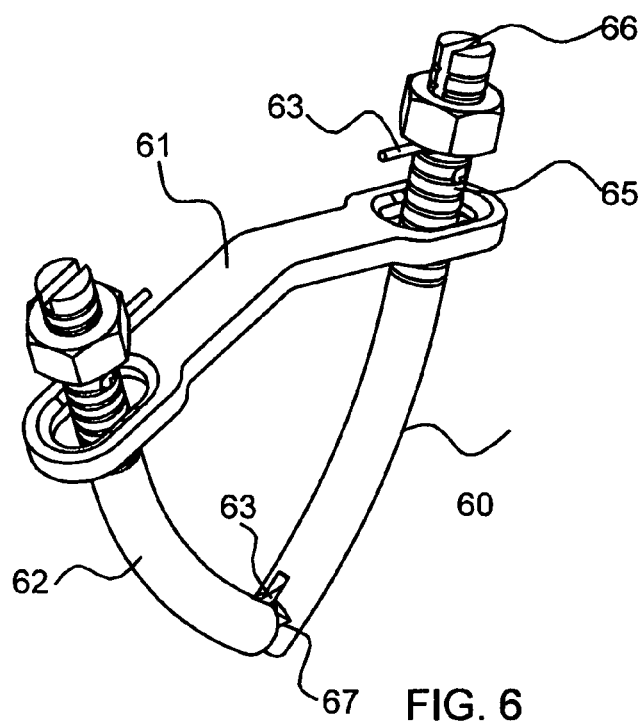
FIG. 6 illustrates a pair of cannulated arcuate elements, with a fixation cord running through and between them.

Referring first to FIG. 6, there is shown a pair of cannulated arcuate elements 60, 62, with the fixation cord 63 running through and between them. A cross member 61 completes the triangular structure, and may be locked onto the bone into which the arcuate elements are inserted by means of a nut (not shown in FIG. 6) screwed onto the threaded extremities 65 of the elements. In the example shown in FIG. 6, the end of the cord 63 protrudes from a slit 66 in the end of the arcuate elements, and is thus clamped into place by closure of the nut onto the cross member 61. At the vertex of the triangular structure, there is shown in this example, a step and shoulder joint 67, which enables the two elements to pivot mutually, until locked into position by the tensioning and locking of the cord 63.

Reference is now made to FIG. 7, which shows schematically further exemplary features illustrated in a pair of cannulated arcuate elements 70, 72, for use in the various implementations described in this disclosure. The arcuate elements differ from those shown previously in that at least part of their length can have step-like or ridge-like features 74. The elements slip readily into the pre-prepared channel in the bone, but once in place, growth of bone around the elements and into the ridges or steps assists in locking the elements into place. The steps or ridges are shown in FIG. 7 applied only near the proximal end of the elements, and only on two opposing sides of the circumference of the elements, but it is to be understood that this is only one exemplary manner of applying the steps or ridges, and that they can equally well be applied over the whole length of the elements, or over the whole girth, or any combination thereof.

Another exemplary feature shown in FIG. 7 is an additional anchoring aid in the form of a winged deployable washer device 73 disposed at the vertex of the triangular structure between the two arcuate elements. This washer device can be constructed in the form of an expanded tubular or even spherical element, preferably made of a sheet material which can be readily bent as the device is crushed. It is slid onto the wire between the two elements and is of sufficiently small diameter that it fits down the channel with the arcuate elements. Application of pressure by tensioning of the cord crushes or crimps the expanded tubular or spherical element between the arcuate element ends, such that as it collapses, the washer wings expand outwards to their deployed size. The winged protrusions of this washer device then have a larger diameter than the preformed channels, and bite into the surrounding bone to provide additional clamping of the triangular structure in the bone.

In the exemplary structure shown in FIG. 7, there is also seen a method of attachment of the distal ends of the arcuate arms to the cross member (not shown), and to the external structure (not shown) using a polyaxial mounting head 75. Such a head, as is known in the art, is able to pivot about a range of angles until locked, such that the cross member and externally attached structures can adopt their most natural pose before the structure is locked. The external cross member can be bridged along the end surfaces 76 of the arcuate elements, and attached by means of a locking nut and stud, or a screw inserted into the threaded end bore 77. Furthermore, a connecting rod to a neighboring vertebra can be inserted through the bore 78, and also fixed by this locking nut or screw. Locking of the tensioning cable can be achieved by means of a crimped end 79 to the cable.

Reference is now made to FIG. 8A, which schematically illustrates further exemplary features in a pair of cannulated arcuate elements 80, 82, for use in the various implementations of triangular structures described in this disclosure. The exemplary elements shown in FIG. 8A have ridges 84 along the major part of their length, though they could also be smooth. However, at the proximal end of the elements, there is a straight sleeve 85 with a threaded external surface 86, which can rotate on the core of the proximal end of the arcuate element. One method of rotating the sleeve 85 is by means of a specially shaped washer 87 attached to the proximal end of the sleeve. As the washer 87 is rotated, the sleeve 85 also rotates while the arcuate element core may be held stationary, such as by use of an Allen key engaging an Allen socket 88 in the end of the element. The arcuate element is inserted into the preformed channel in the bone up to the beginning of the threaded sleeve 85. Rotating the sleeve then results in the sleeve screwing itself into the bone as the spiral external screw thread 86 cuts a path in the inner wall of the preformed passage, analogously to a self-tapping screw. This screwing action thus draws the insert into the passage, until the distal end of the arcuate element reaches the apex of the preformed passages. This feature thus assists in the insertion and anchoring of the elements into the bone.

Reference is now made to FIG. 8B which shows schematic details of an alternative device and method of providing positive anchoring of an arcuate element in its preformed channel. In place of the helically threaded sleeve of FIG. 8A, FIG. 8B shows a split collar 89 with sharp ridge profiles 81 formed on its outer surface. The collar has an inner diameter which is designed to fit tightly over the neck of the arcuate element 83. The collar has an outer diameter, as measured over its ridged teeth, which can fit into the preformed channel in the bone, only if the collar is compressed slightly as it is inserted. The slit in the collar enables this compressing action. In use, the collar is pinched and inserted into the neck of the preformed channel, and the arcuate element 83 is forced into the internal bore of the collar 89. As the arcuate element is forced in, it expands the collar radially outwards, such that the ridged teeth 81 bite into the bone, anchoring the arcuate element securely into its preformed channel. Once the collar is firmly embedded in the bone, the arcuate element may be fixed to the collar by any suitable mechanical fixing device, such as by a sleeve-nut which fits within the cup at the top of the collar, and screws onto a threaded end of the arcuate element. This nut could be an integral part of the poly-axial head shown in FIG. 7.

The threaded sleeve of FIG. 8A and the split collar of FIG. 8B have so far been described as an additional feature for assisting in the anchoring (and entry in the case of the threaded sleeve) of the arcuate elements described hereinabove. However, since these implementations provide a positive locking action for the arcuate elements, according to another exemplary aspect of the invention of the present application, it may be possible to forgo the need for the tensioned wire, and to rely on the screwed sleeve or the split collar to provide the additional forces to ensure positive and effective anchoring of the arcuate elements in the bone.

Figure 9A:
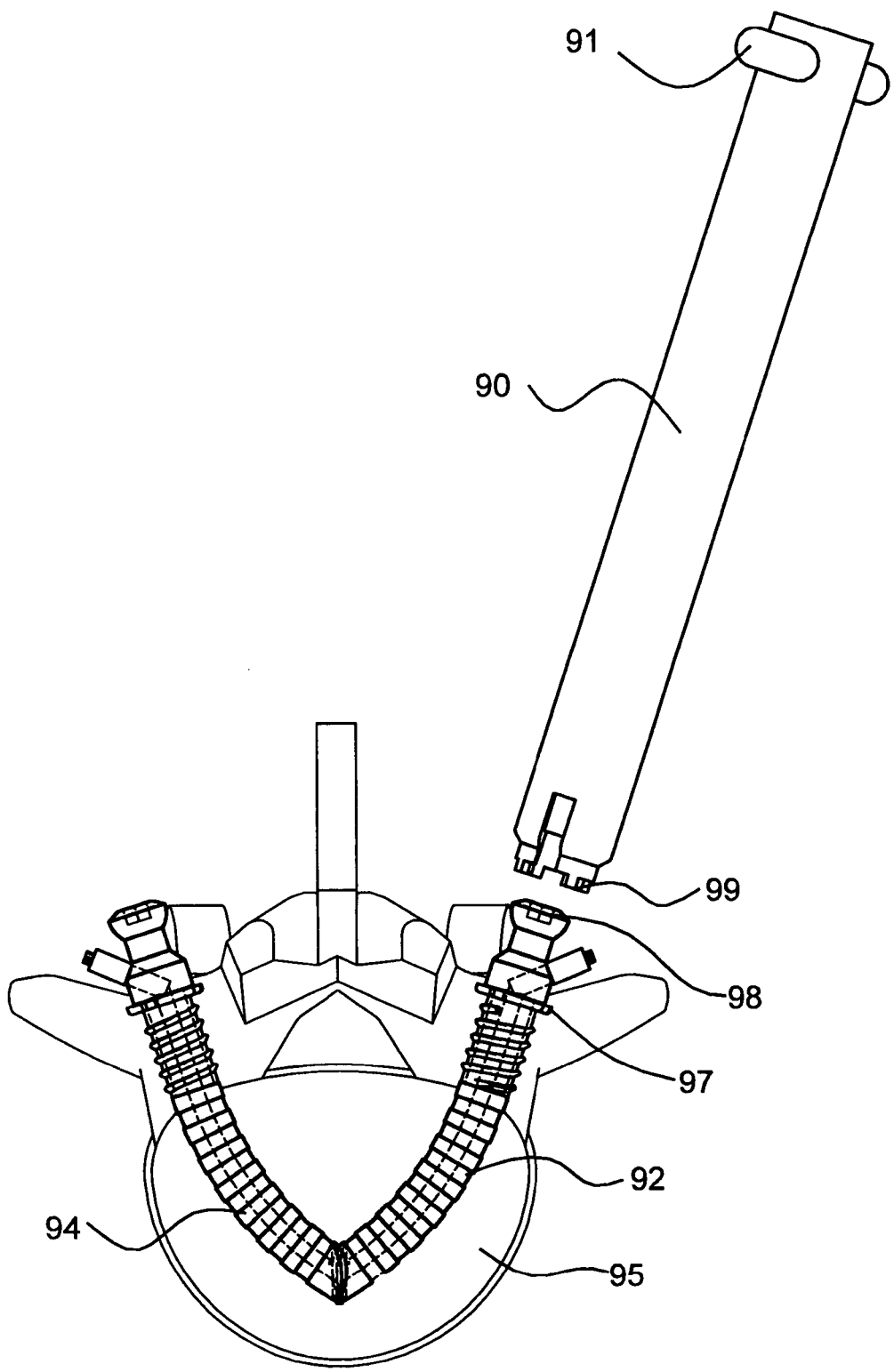
FIGS. 9A and 9B show schematic details of a screwdriver type of tool useful for inserting the rotatable screw sleeve elements of FIG. 8A into a vertebra.
Figure 9B:
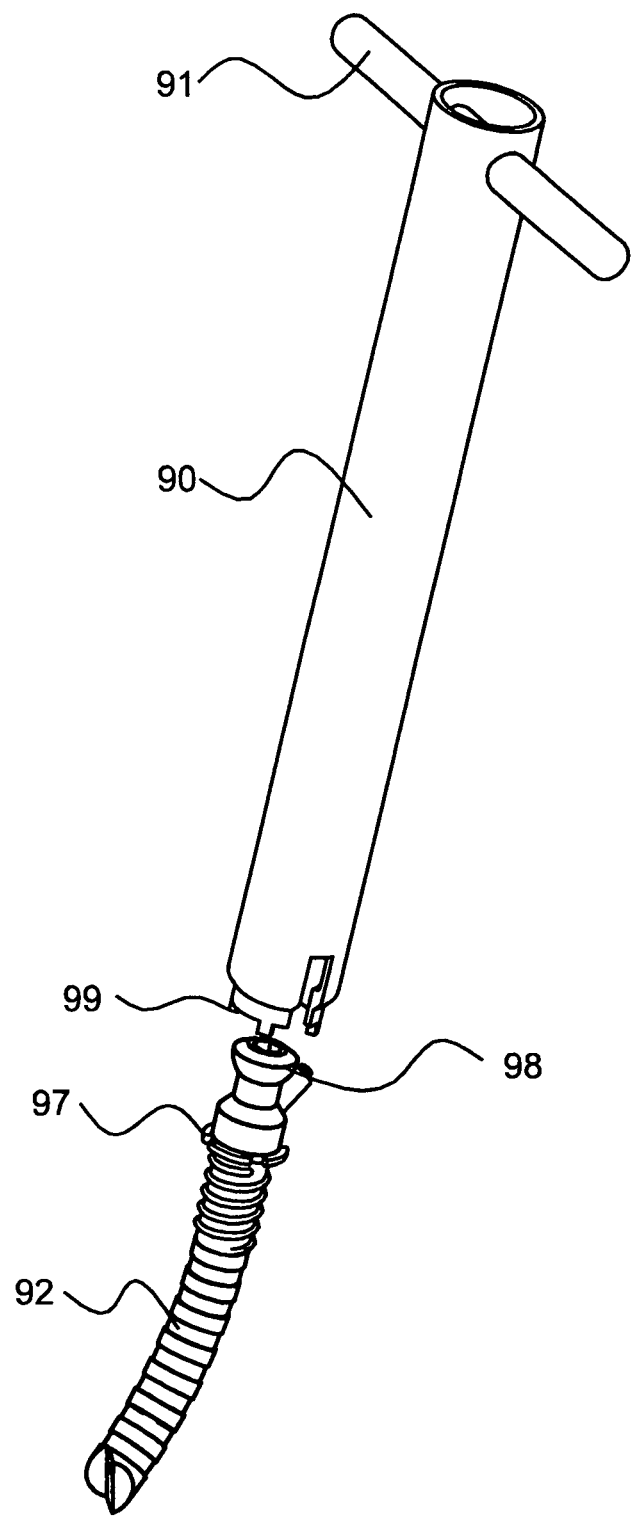

Reference is now made to FIGS. 9A and 9B which show schematic details of a screwdriver type of tool 90 useful for inserting the elements of FIG. 8 into a vertebra. FIG. 9A shows a cross section of the vertebra 95 with the arcuate elements 92, 94, inserted, while FIG. 9B shows an isometric view of the tool 90 and an arcuate element 92. The tool may have a tubular construction with a handle 91 for turning it. The bore should be hollow to enable insertion of an Allen key into the Allen socket head 98 of the arcuate element core. The bottom end of the tool shown in FIGS. 9A and 9B has a series of teeth 99 which can mate with the specially shaped washer 97, thus enabling the washer 87 and hence the screwed sleeve 95 to be turned to insert the arcuate element. Any suitable alternative method of turning the sleeve can be used in order to insert it. As one such example, the proximal end of the sleeve could have a hexagonal head, such as a nut, attached, which could be turned by use of a regular open ended wrench. Any other suitable turning arrangement could also be envisaged for use with this implementation.

Figure 10:
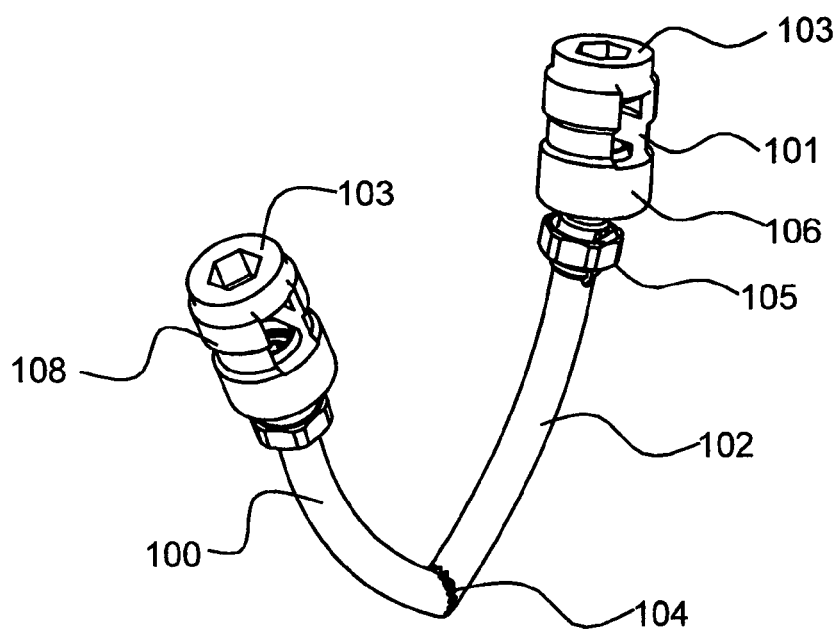
FIG. 10 illustrates schematically another set of arcuate elements whose distal ends are provided with matching teeth structures, such that the elements are locked together in one degree of freedom.

Reference is now made to FIG. 10, which schematically illustrates further exemplary features in a pair of cannulated arcuate elements 100, 102, for use in the various implementations of triangular structures described in this disclosure. In the examples shown in FIG. 10, the distal ends of the arcuate elements are provided with matching teeth structures 104, such that the two elements are locked together in one degree of freedom, namely that of mutual rotation, even without the cable being tightened. The heads 106, 108 of the arcuate elements are of the poly-axial design, such that they do not need to take up a predefined position relative to the elements. The head may have a locking device, such as a screw head 103 for locking to the element an external structure inserted into the aperture 101, while the tensioning cord may be locked by means of an additional fixing device, such as a lock nut 105.

Triangular structures according to any of the above mentioned examples, in adjacent vertebrae may be connected by means of cross members, such that the two vertebrae are fused together. The triangular structures in each of the two separate vertebrae constitute rigidly anchored structures, which may then be connected to each other in any suitable manner to generate a rigid structure fusing the adjacent vertebrae. The cross members may be in the form of parallel links, connecting the left side of one vertebra with the left side of its neighbor, and the right side with the right, or they could be in an H-form or in an X-form to provide additional mechanical stability. According to further such methods, it is not essential that a base member is used for the triangular structure of either of the adjacent vertebrae. Thus, for the exemplary arrangement of two adjacent vertebrae, each having a pair of arcuate elements, such as in FIG. 5A, real triangular structures need not be created, but instead, the base member 58 could be connected vertically to the pedicle on the structure on the adjacent vertebra, such that each "base side" is connected between two separate structures, the first base side between the two cannulated arms that extend from the two left pedicles, namely the left pedicle of the upper vertebra and the left pedicle of the lower vertebra, and the second base side, between the two cannulated arms that extend from the right pedicles. Another member may be connecting between the two separate base sides to generate an H shape, or the base sides connected in an X shape. The combined and interlocked structure becomes a rigid binding harness that firmly connects the two adjacent vertebrae to one another, minimizing movement between them, as is required in spinal fusion procedures.

Reference is now made to FIGS. 11 to 14 which are schematic isometric views of a triangular structure used for connecting adjacent vertebrae, by means of wire-stabilized, transvertebral arcuate elements of the types described hereinabove. In these figures, and in FIG. 15, in order to make the structures themselves clearer, they have been brought to the foreground of the drawings so that the outlines of the numerous features of the overlying vertebrae do not confuse the form and location of the structures. Two independent triangular structures, one on each side of the spine, and each of which runs from one vertebra to its adjacent vertebra, are inserted across the intervertebral space. Each of the triangular structures has one cannulated arm inserted into one vertebra and another cannulated arm inserted into the neighboring vertebra, and they may meet and make contact between their distal ends in the intervertebral space, or in one of the vertebral bodies if a non-symmetrical configuration is used. In this embodiment, the base side bridges posteriorly between the adjacent vertebrae when connected to the proximal ends of each pair of cannulated arms. Passages are created on either side of the spine, each a result of two intersecting tunnels. The two passages are roughly parallel to one another, one on either side of the spinal column. The entrance points of each of the tunnels are preferably at the pedicles, which by their nature, have roughly the mutual angle and course such that a tunnel can be drilled down them through their osseous canal, into the vertebral body, and towards the vertebra's anterior side at its midline. Unlike the previous embodiments of FIGS. 5A and 5B, where the tunnel is aligned in an approximately horizontal posterior-anterior direction, in this embodiment, the tunnels are tilted towards the neighboring vertebra, such that each is aligned to intersect with the tunnel from the adjacent vertebra in the intervertebral space, or nearby thereto.

More specifically, taking the left side as an example, the tunnel at the upper vertebra is drilled aligned down towards the lower end plate of its vertebra and the lower tunnel is aimed up towards the upper end plate of its vertebra, both being aimed to intersect one another at the intervertebral space, to create an apex of the triangle at their intersection point. The combined passage is the combination of the two tunnels, each being one side of the left hand triangular structure such that a vertex is formed by the intersection of these two sides. This procedure is then repeated on the other side of the vertebrae. The method further includes the step of passing a flexible cable through the combined passage so that it protrudes from the two entrance points, these being the left pedicles of the neighboring vertebrae. This step, and each of the following steps, is then repeated for the right side. The method then includes the step of inserting the two cannulated arms, sliding over the cable, each arm advancing from its respective entrance into its respective tunnel. The cannulated arms advance into the vertebral bone tunnels, to the point of intersection of the tunnels, where the arms make contact at their distal ends and create an apex. The cable is then tightened and locked at the proximal ends that protrude from the bone, in this example, at the pedicles. This procedure secures the contact between the cannulated arms at the vertex but also allows the arms to flex, allowing small change of angle between them, and hence between the vertebrae in which they are embedded. As a result, the cannulated arms which extend from the pedicles of the two adjacent vertebrae may function as lever arms, and by adjusting the angle between the arms, the surgeon may control the posture between the adjacent vertebrae. This may be used to enforce a desired posture between the adjacent vertebra, such as the level of lordosis, kyphosis and height, when using the implant also to treat spinal deformities. Once these parameters are optimally adjusted, the base side of the triangular structure may be connected to the extended ends of the arms, to maintain the desired posture. If necessary, a spacer or cage may be positioned between the vertebrae to assist in support of posture and intervertebral height.

Figure 11:
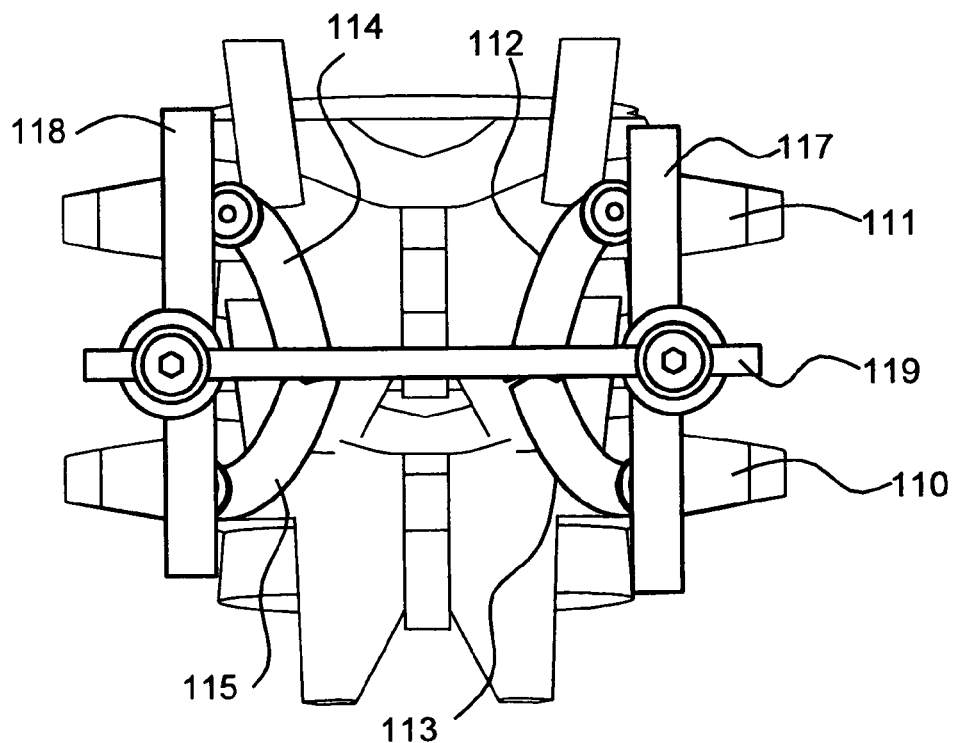
FIGS. 11 to 14 are schematic elevation, plan and isometric views of triangular structures used for connecting adjacent vertebrae, by means of wire-stabilized, transvertebral arcuate elements of the types described in FIGS. 5A to 10.

Referring now to the details of FIGS. 11 to 14, in FIG. 11, which is a posterior view of the arrangement, the two adjacent vertebrae 110, 111, are stabilized by two such triangular structures. The structures used are vertically aligned pseudo-triangles, one on each lateral side of the vertebrae, a right hand triangular structure made up of arcuate elements 112 and 113, and a left hand triangular structure made up of arcuate elements 114 and 115. Each pair of arcuate elements are shown meeting in the intervertebral space. The third sides of the triangular structures are shown ready for connection by vertical rod 117 on the right hand side of the spine, and rod 118 on the left hand side of the spine. These base elements 117 and 118 are shown connected laterally by a connecting rod 119, thus strengthening the entire structure. The base elements 117 and 118 could alternatively be crossed in an X-shape, such that they serve the functions both of connecting adjacent vertebrae, and also of supplying lateral rigidity. Although the arcuate elements are shown meeting at an apex in the intervertebral space, it is to be understood that the method can equally well be used for meetings within one of the vertebral bodies, in which case each of the arcuate arms in the pairs on each side of the spine, 112 and 113, or 114 and 115, would not be of equal length. In all of FIGS. 11 to 14, in order to increase the clarity of the drawings, the connecting rods 117, 118 are shown detached from the polyaxial heads of the arcuate elements, but in position ready to be attached thereto.

Figure 12:
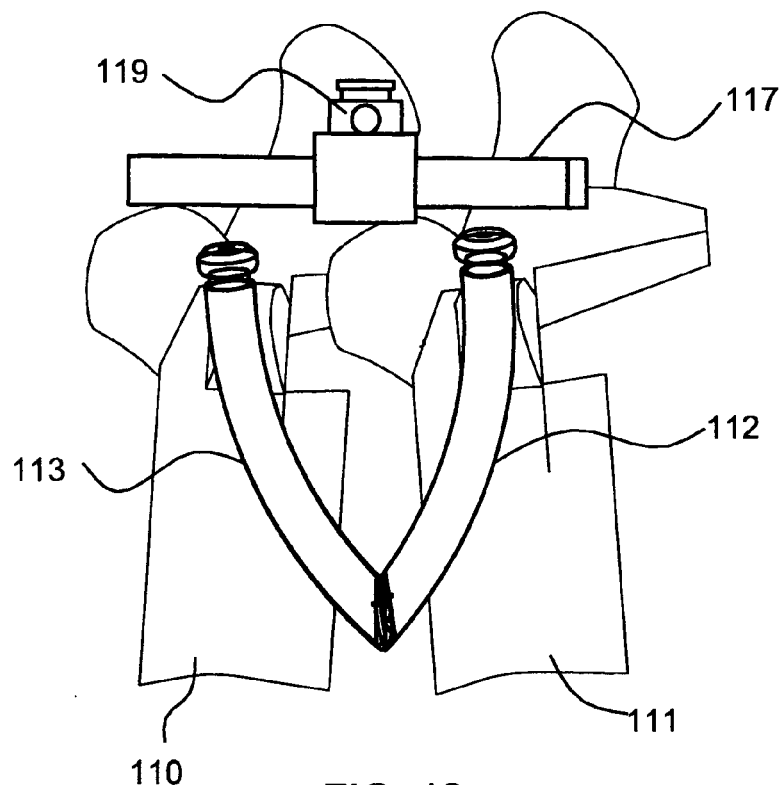
Figure 13:
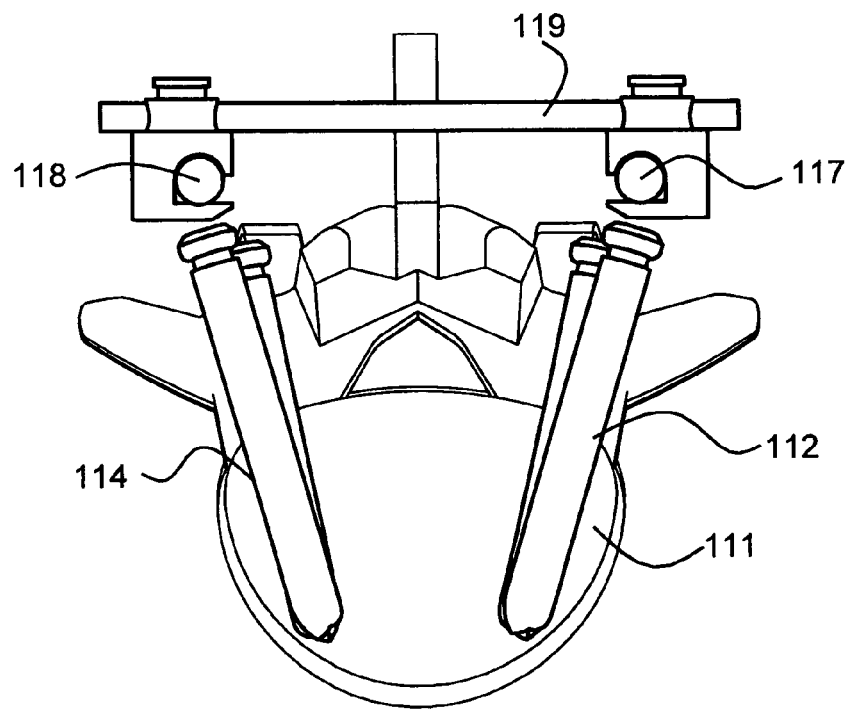
Figure 14:
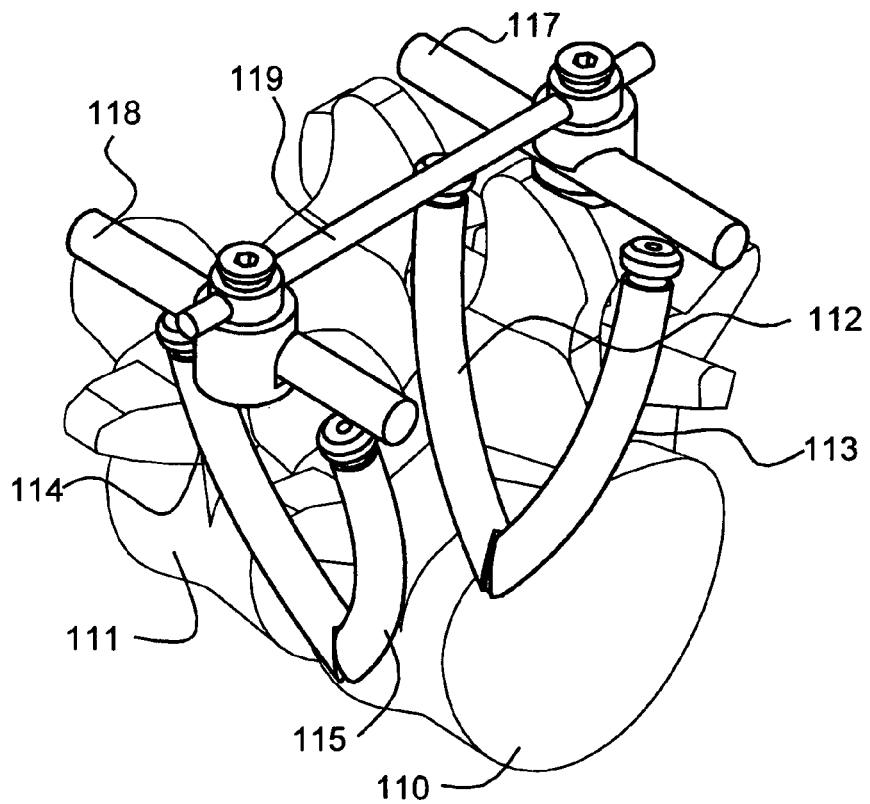

FIG. 12 is a schematic lateral view of the transvertebral connecting arrangement of FIG. 11, in which the apex of the triangle is in the intervertebral space; FIG. 13 is a top view thereof; and FIG. 14 is an isometric view showing the arrangement of all four of the arcuate elements together. In these four representations, like reference characters are used for the same elements.

Figure 15:
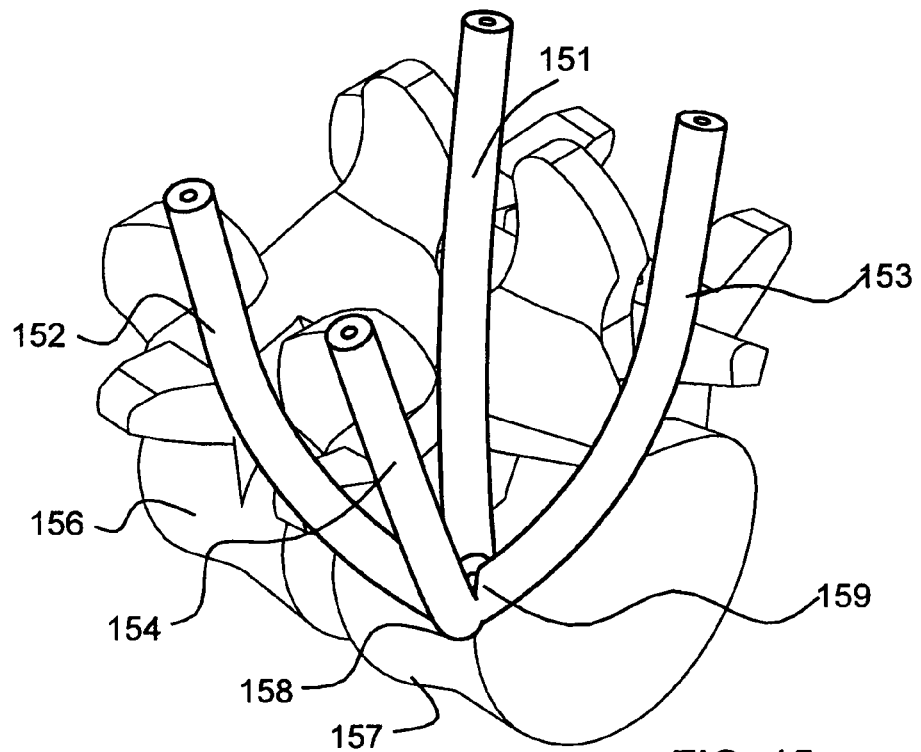
FIG. 15 is an isometric schematic view of a pair of vertebrae connected by arcuate triangular structures which connect both laterally and vertically by crossing paths within the intervertebral region or nearby thereto.

According to yet a further preferred embodiment of the above method, the drilling of the tunnels, whether straight or arcuate, is aimed to cross the vertebrae at an angle and on a path that positions the opposite ends of the complete passage on alternate sides of the neighboring vertebrae. Such an arrangement is shown in FIG. 15, which is a schematic computer rendering of a pair of vertebrae 156, 157 connected by arcuate triangular structures which connect both laterally and vertically by crossing paths within the intervertebral region 158, or nearby thereto. More specifically, the arcuate element 152 starting at the left pedicle of the upper vertebra 156, is joined to the arcuate element 153 starting at the right pedicle of the lower vertebra 157, so that the triangular structure connects the upper left pedicle to lower right pedicle with a vertex at the intervertebral space 158 at about the anterior midline, or within one of the vertebral bodies near that point. The triangular structure is thus aligned such that it is tilted in both planes, horizontal and vertical. In this method, the second passageway, for the second triangular structure, is an approximately mirror image of the first passageway, with the arcuate arm 151 connecting from the upper right pedicle to the arm 154 from the lower left pedicle, with a vertex within the intervertebral space 159, at about the anterior midline, or within one of the vertebral bodies close thereto. The third base side of each triangular structure is attached to the two proximal ends of the two cannulated arms of each triangular structure. Because of the crossed over orientation of the two triangular structures, their base sides may preferably be installed to intersect, such that a base element is connected between ends 151 and 154, and another between ends 152 and 153. This allows combining the two triangular structures by connecting the two base sides to each another at their point of intersection, thus providing an even more robust method of vertebral fusion. Although the apexes of each of the two crossed-over triangular structures are shown in FIG. 15 situated in the intervertebral space, according to further implementations of the present invention, the apexes could also be situated in an intravertebral space, if the triangular structure geometry is so arranged asymmetrically.

Figure 16:
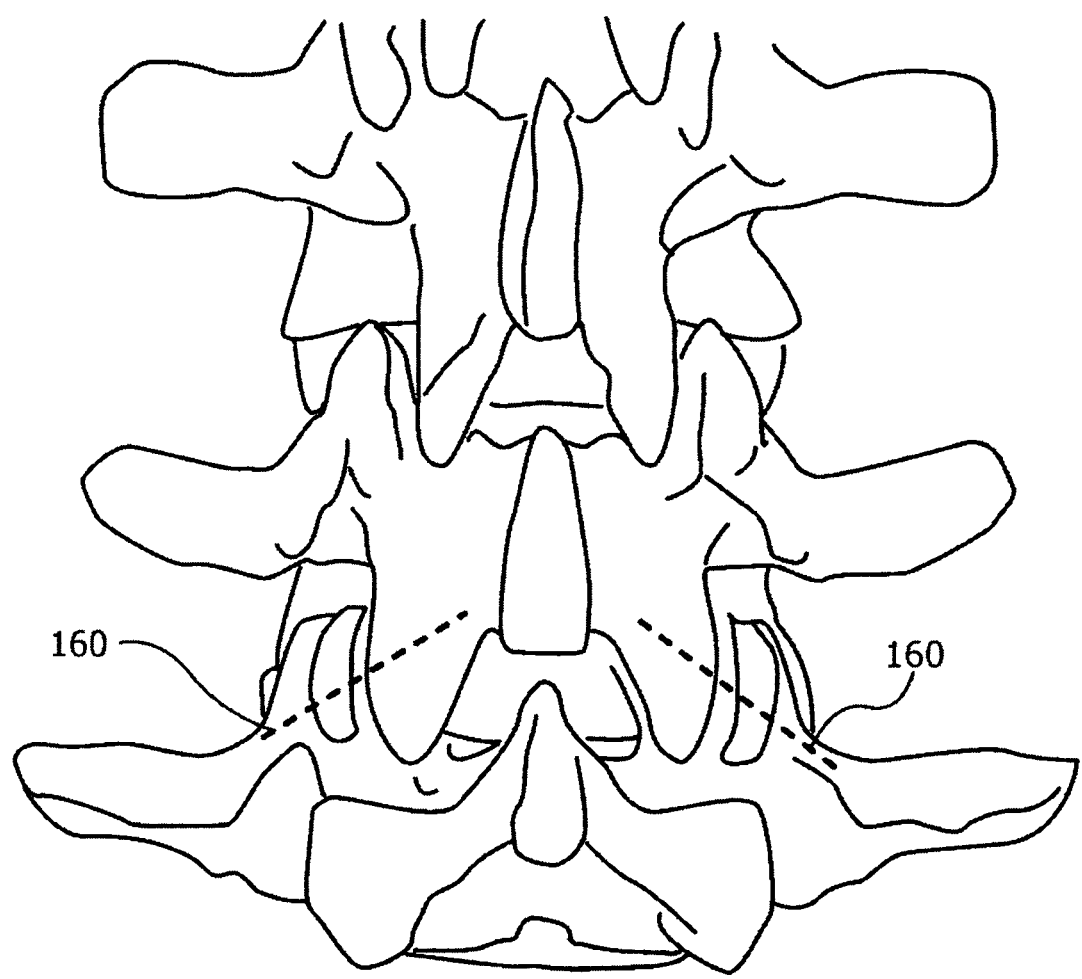
FIG. 16 illustrates schematically the use of triangular structures for trans-facet joint fixation.

Reference is now made to FIG. 16, which illustrates schematically the use of triangular structures such as those described hereinabove, for trans-facet joint fixation. According to these embodiments, stabilizing and fixating of two adjacent vertebrae can be performed by immobilizing and stabilizing the facet joint. This is done by inserting the sides of the triangular structure through and across each of the lamina and facet joints between adjacent vertebrae. Each of the triangle structures has one cannulated arm inserted into its respective lamina (left side lamina and right side lamina) and the other arm inserted into the pedicle of the adjacent vertebra to cross the facet joint. The two cannulated arms of the triangle are arranged to contact one another with their distal ends at the facet joint plane. In this embodiment, the base side posteriorly bridges between the lamina and pedicle of the adjacent vertebrae when connected to the proximal ends of the cannulated arms. This is shown in FIG. 16. This method includes the steps of creating the two passages, each a result of two intersecting tunnels. The left passage, for instance, is a combination of two tunnels, one in each of the adjacent vertebra. The upper tunnel starts at the upper vertebra, at the left lamina, close to the Spinous Process. There it penetrates the cortical bone and runs through the lamina towards the facet joint. This upper tunnel is preferably arcuate. The lower tunnel starts at the pedicle of the lower vertebra, in a direction and angle such that it crosses the facet joint. The lower tunnel may be straight or arcuate. Both tunnels are aimed to intersect one another at the facet joint, to create the vertex of the path of the triangular structure at this point. The combined passageway is the combination of the two tunnels, each being one of the sides of the left hand triangular structure, such that a vertex is formed at the facet joint by the intersection of these two sides. The same construction is repeated on the right side. FIG. 16 is a posterior view of the spine, showing a facet joint 160, and with dashed lines indicating the direction across the facet joints where the triangular structure is to cross the facet joint. The method further includes the step of passing a flexible cable through the combined passageway so that it protrudes from the two entrance points. Then, the method includes, for each side, the step of inserting two cannulated arms over the cable, each arm being advanced from its respective entrance into its respective tunnel. The cannulated arms are pushed into the vertebral bone tunnels, up to the point of intersection of the tunnels, were the arms make contact at their distal ends and create a vertex. The cable is tightened and locked at the proximal ends that extend from the bone. This secures the contact between the cannulated arms at the vertex. Then, the base side is connected to the extending sections of the arms, to achieve the triangular structure. If necessary, a spacer may be positioned inside the facet joint, to assist in maintaining the desired posture and to assist fusion.

Figure 17:
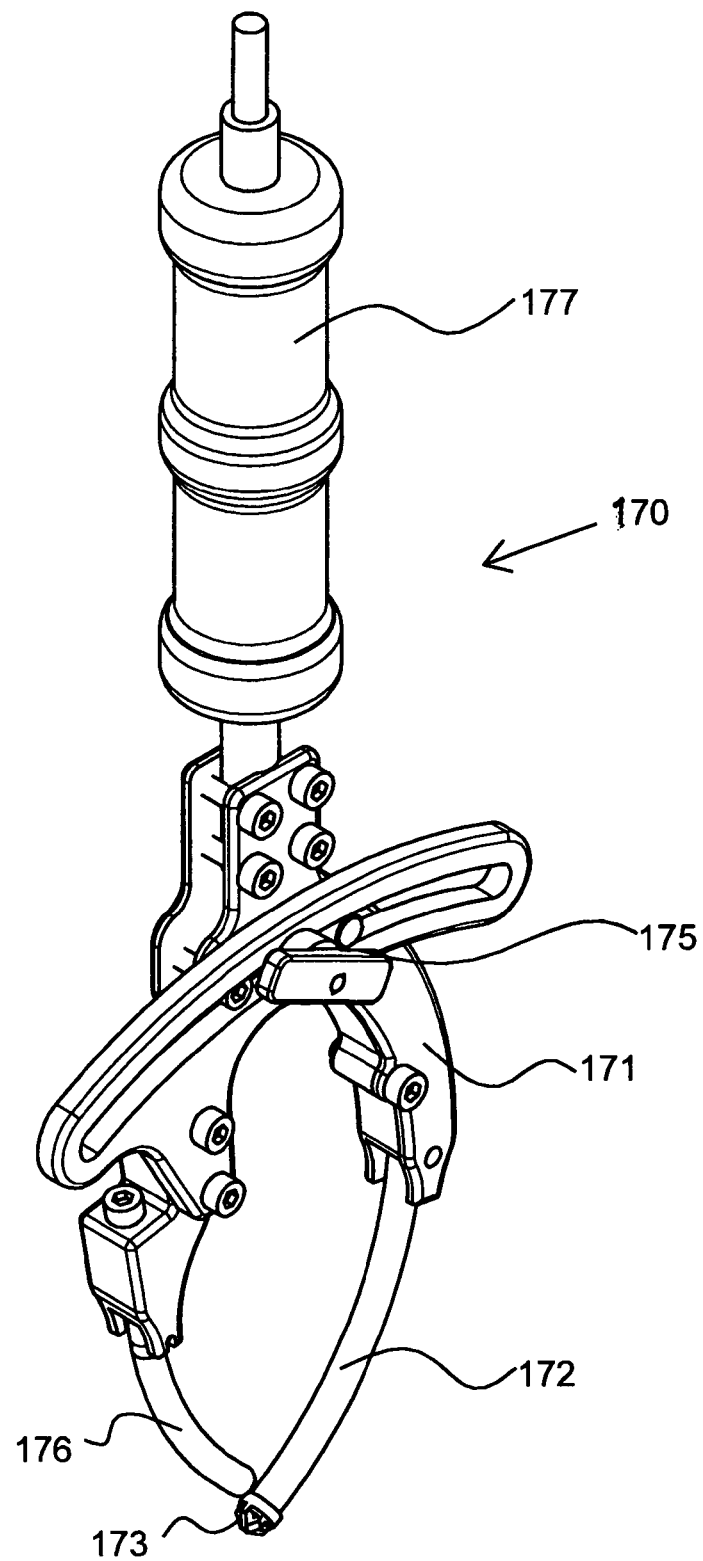
FIG. 17 is a schematic illustration of an exemplary tool to generate the preformed arcuate passageways in the bone to be fixated, and especially in a vertebra.

Reference is now made to FIG. 17, which is a schematic illustration of an exemplary tool 170 which may be used to generate the preformed arcuate passageways in the bone to be fixated, and especially in a vertebra. The tool may comprise a curved lead channel 171 with an arcuate hollow drill guide 172 attached to its lower end. The drill bit 173, on a flexible drilling cable, can be seen at the base end of the drilling guide 172. An adjustable alignment assembly 175 is provided to adjust the position of the drilling guide 172, relative to the center line of the tool. A counter probe 176 is used to ensure that the drilling guide maintains its correct predetermined position. The counter probe may advantageously have an arcuate shape matched to that of the arcuate hole to be drilled. In use, a small starting hole is drilled separately in each pedicle, and the drilling tip 173 and the tip end of the counter probe 176 are inserted into these two starting holes. The counter probe 176 holds the tool stably while the arcuate hole is drilled into the opposite pedicle. Once the first pedicle passageway is completed, the tool is removed, and the counter probe 176 is inserted into the completed hole while the other pedicle arcuate passageway is now drilled, the tool being firmly stabilized by the counter probe inserted into the first. A handle 177 is provided to hold the tool steadily during the drilling process.

It is to be understood that the methods, systems and devices of the present disclosure are not meant to be limited to securing a pair of vertebrae, but can also be used for any combination of multiple vertebrae segments. It is also to be understood that these methods, systems, and devices are not intended to be limited to vertebrae segments. In particular, these methods, systems, and devices enable the securing of any solid substrates, particularly bone substrates, without the use of protruding screws or plates. It should also be understood that they are applicable to a wide variety of fixation configurations, including bone-to-bone with a gap; bone-to-bone without a gap; bone-to-bone with bony spacers; and bone-to-bone with a non-bony spacer such as a metal, polymer, or a biodegradable material.

Although preferred embodiments of the invention have been described using specific terms, such description is for illustrative purposes only, and it is to be understood that changes and variations may be made without departing from the spirit or scope of the claims, which follow.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A method for stabilizing adjacent vertebrae of a spine, comprising the steps of:
    forming a first arcuate passage in a first one of said vertebrae from a pedicle entry point to an intra-vertebral anterior position;
    forming a second arcuate passage in said first vertebrae from the opposite pedicle entry point to meet said intra-vertebral anterior position;
    threading a wire between said pedicle entry points;
    sliding an arcuate cannulated member into each of said arcuate passages;
    tensioning said wire such that said ends of said arcuate members become tightened onto a junction at said intra-vertebral anterior position;
    repeating said steps on a second vertebra adjacent to said first vertebra; and
    fixating said first and second vertebra by rigidly connecting at least one pair of pedicular ends of said cannulated members between said first and second vertebrae.

2. A method according to claim 1 further comprising the step of attaching said wire to the ends of said arcuate cannulated members after tensioning of said wire.

3. A structure according to claim 1 and wherein at least one of said cannulated members further comprises a straight threaded rotatable sleeve mounted on a proximal part of its length, such that when said sleeve is rotated, said thread becomes screwed into said bone region associated with said at least one cannulated member.

4. A method for stabilizing adjacent vertebrae of a spine, comprising the steps of:
    forming a first arcuate passage in a first one of said vertebrae from a pedicle entry point to an anterior position;
    forming a second arcuate passage in a second vertebra adjacent to said first vertebra, from a pedicle entry point on the same lateral side of said vertebra as that of said first vertebra, to meet said anterior position of said first arcuate passage;
    threading a wire between said pedicle entry points;
    sliding arcuate cannulated members down each of said arcuate passages;
    tensioning said wire such that said ends of said arcuate members become tightened onto a junction at said anterior position;
    repeating said steps on the opposite lateral side of said first and second vertebra; and
    fixating said first and second vertebra by rigidly connecting at least one pair of pedicular ends of said cannulated members between said first and second vertebrae.

5. A method according to claim 4 further comprising the step of attaching said wire to the ends of said arcuate cannulated members after said tensioning of said wire.

6. A method according to claim 4 wherein said anterior position is either one of inter-vertebral or intra-vertebral.

7. A structure according to claim 4 and wherein at least one of said cannulated members further comprises a straight threaded rotatable sleeve mounted on a proximal part of its length, such that when said sleeve is rotated, said thread becomes screwed into said bone region associated with said at least one cannulated member.

8. An orthopedic structure, comprising:

a first cannulated element configured to be disposed for at least a major part of its length within a first bone region of a subject and a second cannulated element configured to be disposed for at least a major part of its length within a second bone region of a subject, said first and second elements being disposed respectively from first and second entry points, to a junction at which their distal ends meet, at least one of said cannulated elements being arcuate in form and configured to be disposed in a preformed arcuate passage in its bone region; and a wire threaded through both of said cannulated elements between their proximal ends, such that when said wire is tensioned, said distal ends of said first and second cannulated elements become tightened onto said junction, such that said first and second cannulated elements are configured to generate a rigid structure within said first and second bone regions, wherein the proximal ends of said cannulated elements are rigidly connected to form a three sided triangular structure either by means of a rigid connecting element, or by being configured to be attached to posterior parts of said bone regions, and wherein said first and second cannulated elements are located in a single vertebra, such that said three sided triangular structure is an anchor for fixation of said single vertebra to an adjacent vertebra.

9. A structure according to claim 8 and wherein at least one of said cannulated elements further comprises a straight threaded rotatable sleeve mounted on a proximal part of its length, such that when said sleeve is rotated, said thread becomes screwed into said bone region associated with said at least one cannulated element.

10. An orthopedic structure, comprising:

a first cannulated element configured to be disposed for at least a major part of its length within a first bone region of a subject and a second cannulated element configured to be disposed for at least a major part of its length within a second bone region of a subject, said first and second elements being disposed respectively from first and second entry points, to a junction at which their distal ends meet, at least one of said cannulated elements being arcuate in form and configured to be disposed in a preformed arcuate passage in its bone region; and a wire threaded through both of said cannulated elements between their proximal ends, such that when said wire is tensioned, said distal ends of said first and second cannulated elements become tightened onto said junction, such that said first and second cannulated elements are configured to generate a rigid structure within said first and second bone regions, wherein the proximal ends of said cannulated elements are rigidly connected to form a three sided triangular structure either by means of a rigid connecting element, or by being configured to be attached to posterior parts of said bone regions, and wherein said first and second cannulated elements are disposed for at least a major part of their lengths in adjacent vertebrae, such that said three sided triangular structure is configured for fixation of said adjacent vertebrae.

11. A structure according to claim 10 wherein said first and said second entry points are disposed on opposite sides of the spine of said subject, such that when said first and second cannulated elements are disposed in said bone regions, they are diagonally disposed relative to the spine of said subject, such that said structure is operative for fixation of said vertebrae to each other.

12. A structure according to claim 10 and wherein at least one of said cannulated elements further comprises a straight threaded rotatable sleeve mounted on a proximal part of its length, such that when said sleeve is rotated, said thread becomes screwed into said bone region associated with said at least one cannulated element.

* * * * *